United States Patent [19]

Quadro

[11] Patent Number: 5,312,825
[45] Date of Patent: May 17, 1994

[54] S-(2-THENOYL)-THIOLACTIC ACID DERIVATIVE HAVING PHARMACOLOGICAL ACTIVITY

[75] Inventor: Giuseppe Quadro, Milan, Italy

[73] Assignee: Yason S.r.l., Milan, Italy

[21] Appl. No.: 923,959

[22] PCT Filed: Feb. 28, 1991

[86] PCT No.: PCT/EP91/00366
§ 371 Date: Sep. 3, 1992
§ 102(e) Date: Sep. 3, 1992

[87] PCT Pub. No.: WO91/13883
PCT Pub. Date: Sep. 19, 1991

[30] Foreign Application Priority Data

Mar. 5, 1990 [IT] Italy .................. 19566 A/90

[51] Int. Cl.⁵ .................. C07D 417/12; A01K 31/425
[52] U.S. Cl. ........................... 514/365; 548/201
[58] Field of Search ................... 548/201; 514/365

[56] References Cited

U.S. PATENT DOCUMENTS

| | | | |
|---|---|---|---|
| 4,261,895 | 4/1981 | Wiskott | 548/533 |
| 4,483,801 | 11/1984 | Iwao | 548/201 |
| 5,053,414 | 10/1991 | Toda | 548/201 |

*Primary Examiner*—Robert Gerstl
*Attorney, Agent, or Firm*—Bucknam and Archer

[57] ABSTRACT

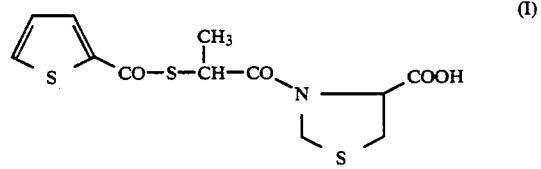

Compound of formula (I) which can be prepared by reacting S-(2-thenoyl)-thiolactic acid and 4-thiazolidinecarboxylic acid, has immunostimulating, antioxidant and mucus regulating activities.

3 Claims, No Drawings

S-(2-THENOYL)-THIOLACTIC ACID DERIVATIVE HAVING PHARMACOLOGICAL ACTIVITY

The present invention relates to the compound of formula I

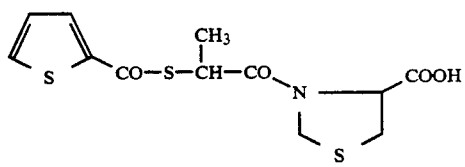

to a process for the preparation thereof and to pharmaceutical compositions containing it.

The invention also relates to the single enantiomers of compound I and to the salts thereof with non toxic bases, such as the sodium, potassium, calcium, lysine, ethanolamine, imidazole salts and the like.

EP-A-120,354 discloses 2-(2-thenoylthio)-N-(3'-tetrahydrothienyl-2-one) propionylamide, which differs from compound I due to the presence of a tetrahydrothienyl-2-one ring instead of the 1,3-thiazolidine ring characterizing the compound of the invention, which moreover has a carboxy group.

The compound described in EP-A-120,354 has bronchosecretogogue (bronchosecretolytic) activity, whereas compound I, which will hereinafter also named YS-3025, beside having mucus regulating activity, also shows other properties, particularly immunostimulating and antioxidant activities, which are unknown in the above cited tetrahydrothiophene derivative.

The results obtained from some pharmacological tests on compound YS-3025 are reported hereinbelow.

IMMUNOSTIMULATING ACTIVITY

The immunostimulating effect of YS-3025 was evaluated by means of the primary antibody response to sheep erythrocytes in mice injected with prednisolone, according to the procedure described by Maestroni and Conti (J. NeuroImmunology 13, 19–30; 1986).

The evaluation of the results, based on the anti-body production (primary response) compared to controls (Yerne's test : Yerne N. K., Henry C., Nordin A. A., Fuj H., Koros A. M. C and Lefkovits J., Transplantation Rev., 19, 130; 1974) evidenced that YS-3025 stimulated to a highly significant degree the primary response to sheep erythrocytes in animals stressed with prednisolone. Antioxidant and free radical scavenger activities The antioxidant activity was evaluated according to different experimental patterns :
protection against doxorubicin toxicity (based on the procedure described by Olson R. D. et al., J. Pharmacol. Exp. Ther., 215, 450; 1980);
protection against acetaldehyde, acrolein and formaldehyde toxic effects (Sprince H. et al., Agents and Actions, 9, 407; 1979).

In all of the tests, YS-3025 proved to have a marked antioxidant activity with a consequent mortality reduction comparable to the one of such other known compounds as N-acetylcysteine and ascorbic acid.

MUCUS REGULATING ACTIVITY

The phenol red test in the mouse was carried out, according to the procedure described by Engler H. et al., J. Pharmacol. Methods, 11, 151; 1984; which test is based on the fact that some dyes can be eliminated through the bronchial tract.

YS-3025 proved to have a higher mucus regulating activity than that of N-acetylcysteine, used as the control drug.

The secretion capability through the respiratory tract was also assessed according to the fluorescein sodium test in the rat, as described by Mawatari H., Kagoshima Daigaku Igaku Zasshi, 27, 561; 1976; modified by Graziani G. and Cazzulani P., Il Farmaco, Ed. Pr., 36, 167; 1981.

YS-3025 proved, also in this test, to have a high effectiveness, comparable to that of N-acetylcysteine.

The above results evidence that YS-3025 can be used in human therapy for the treatment of a variety of conditions, such as bacterial or viral infections, autoimmune diseases, acute or chronic diseases of the bronchopulmonary apparatus. For the envisaged therapeutical uses, YS-3025 will be administered at daily dosages ranging from 50 mg to 1,000 mg, in form of pharmaceutical compositions which can be administered by the oral, parenteral, rectal or topical routes.

Examples of said compositions, which can be prepared by means of conventional techniques and excipients, such as those described in "Remington's Pharmaceutical Sciences Handbook", Hack Pub. Co., N.Y. USA, comprise capsules, dragees, syrups, powders, solutions, vials, suppositories, sustained-release forms and the like.

YS-3025 can be prepared starting from thiolactic acid, by S-acylation with 2-thenoic acid and subsequent reaction with 4-thiazolidinecarboxylic acid. Both the acylation reactions can be carried out by means of the conentional methods used to activate the carboxy group, for example using condensing agents or transforming the carboxy group into such reactive derivatives as acyl halides, mixed or symmetrical anhydrides, imidazolides and the like. S-(2-Thenoyl)-thiolactic acid is known from EP-A-120,354.

The procedures for the salification and the separation of the isomers can also be carried out conventionally.

The following example further illustrates the invention.

EXAMPLE a) A solution of 8.5 g (0.21 mole) of NaOH, 85 ml of water and 10.6 g (0.1 mole) of thiolactic acid is cooled to 5° C. 14.6 g (0.1 mole) of 2-thenoyl chloride are added, keeping that temperature. At the end of the addition pH is controlled to be about 7.8, the mixture is left to react at room temperature for 2 hours, then it is cooled again to 5° C. and acidified to pH 3 with 10% HCl. The product is extracted with methylene chloride; the extract is washed with water, dried over sodium sulfate and evaporated to obtain a thick oily residue which slowly solidifies and it is used directly in the next step. Yield : 19.8 g (91%); m.p. 45°–50° C. NMR spectrum : in conformity.

b) A mixture of 16.4 g of S-(2-thenoyl)-thiolactic acid and 35 ml of thionyl chloride is stirred at room temperature for 12 hours. Thionyl chloride is evaporated off, the residue is taken up with toluene which is then evaporated off. The residue is used as such in the subsequent step.

c) 0.94 g (0.00707 mole) of 4-thiazolidinecarboxylic acid are suspended in 10 ml of ethyl acetate. 2 ml (0.00707×2 mole) of triethylamine and 0.050 g of tetrabutylammonium bromide are added. The mixture is cooled to 5° C. and 1.7 g (0.00707 mole) of S-(2-thenoyl)-thiolactic acid chloride in 10 ml of ethyl acetate are dropped therein. When the addition is over, the mixture is left to react at room temperature for 6 hours. The reaction mixture is treated with $H_2O$/HCl to pH 1. The two phases are partitioned, the organic one is heated for 30 minutes with sodium sulfate and charcoal, then filtered through celite and the solvent is evaporated off. The resulting thick orange oily residue (1.7 g) is crystallized from trichloroethyleee. Compound I is obtained as a colourless solid. Yield : 0.36 g (15%). T.L.C. (toluene/dioxane/AcOH) (45/10/2) unitary; Rf : 0.3, the same as the one from an YS-3025 control sample. M.p. : 159°-161° C. (in admixture with an YS-3025 sample control : 161°-163° C.).

NMR($CDCl_3$) 90MHz($\delta$): 1.65 (d, 3H); 3.4 (d, 2H); 4.55–4.8
(m, 2H); 5.0 (d, 1H); 5.15 (t, 1H); 7.1 (t, 1H); 7.6–7.9 (2d+1s, 3H).

I claim:

1. Compound of formula I

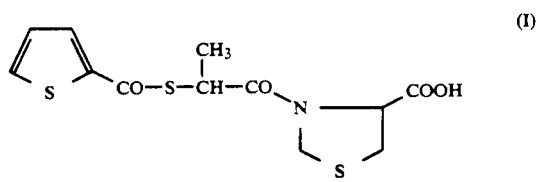

and the non toxic salts and isomers thereof.

2. A pharmaceutical composition in unit dosage form containing as the active ingredient the compound of formula

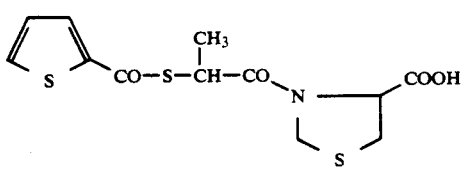

the enantiomer and a non-toxic salt thereof and excipients.

3. The composition according to claim 2 in the form of a capsule, syrup, powder, a solution, a vial, a suppository or in a sustained-release form.

* * * * *